(12) United States Patent
Hill (10) Patent No.: US 8,723,868 B2
(45) Date of Patent: May 13, 2014

(54) SYSTEMS AND METHODS FOR DISPLAYING DIGITIZED WAVEFORMS ON PIXILATED SCREENS

(75) Inventor: Aaron James Hill, Wauwatosa, WI (US)

(73) Assignee: General Electric Company, Schenectady, NY (US)

(*) Notice: Subject to any disclaimer, the term of this patent is extended or adjusted under 35 U.S.C. 154(b) by 817 days.

(21) Appl. No.: 12/888,802

(22) Filed: Sep. 23, 2010

(65) Prior Publication Data

US 2012/0075307 A1    Mar. 29, 2012

(51) Int. Cl.
*G06T 11/20*      (2006.01)

(52) U.S. Cl.
USPC ........... 345/440; 345/441; 345/661; 345/443; 345/581; 345/619; 345/613; 382/118; 382/190; 382/170; 382/173; 382/268

(58) Field of Classification Search
USPC ................. 382/118, 190, 170, 173, 268, 269; 345/441, 611, 443, 581, 619, 613, 440
See application file for complete search history.

(56) References Cited

U.S. PATENT DOCUMENTS

| | | | | |
|---|---|---|---|---|
| 5,461,703 A * | 10/1995 | Goyins et al. | ......... | 358/1.9 |
| 5,815,162 A * | 9/1998 | Levine | ......... | 345/443 |
| 6,674,875 B1 * | 1/2004 | Phillips et al. | ......... | 382/100 |
| 6,947,057 B2 * | 9/2005 | Nelson et al. | ......... | 345/611 |
| 6,985,159 B2 * | 1/2006 | Brown | ......... | 345/611 |
| 7,136,081 B2 * | 11/2006 | Gritz et al. | ......... | 345/619 |
| 7,227,556 B2 * | 6/2007 | O'Driscoll | ......... | 345/611 |
| 2002/0000988 A1 * | 1/2002 | Nelson et al. | ......... | 345/443 |
| 2002/0030683 A1 * | 3/2002 | Alexander | ......... | 345/440.1 |
| 2003/0164840 A1 * | 9/2003 | O'Driscoll | ......... | 345/611 |
| 2003/0210251 A1 * | 11/2003 | Brown | ......... | 345/611 |
| 2004/0260188 A1 * | 12/2004 | Syed et al. | ......... | 600/509 |
| 2006/0072818 A1 * | 4/2006 | Herley | ......... | 382/173 |
| 2006/0120583 A1 * | 6/2006 | Dewaele | ......... | 382/128 |
| 2006/0133571 A1 * | 6/2006 | Winsor | ......... | 378/98.8 |
| 2006/0133694 A1 * | 6/2006 | Dewaele | ......... | 382/294 |
| 2007/0222784 A1 * | 9/2007 | Arneau et al. | ......... | 345/441 |
| 2007/0229527 A1 * | 10/2007 | Moulios | ......... | 345/581 |
| 2008/0009723 A1 * | 1/2008 | Schefelker et al. | ......... | 600/437 |
| 2009/0018897 A1 * | 1/2009 | Breiter | ......... | 705/10 |
| 2009/0079741 A1 * | 3/2009 | Gilbert | ......... | 345/441 |

(Continued)

OTHER PUBLICATIONS

Wu, Xiaolin. "An Efficient Antialiasing Technique." Computer Graphics, vol. 25, No. 4, Jul. 1991.

*Primary Examiner* — Abderrahim Merouan
(74) *Attorney, Agent, or Firm* — McAndrews, Held & Malloy, Ltd.; Eric Severson; Patrick Kim (57) ABSTRACT

Systems and methods for displaying digitized waveform data on a pixilated screen are provided. Certain methods include retrieving waveform data that exists as a plurality of sequential samples in a buffer. A first sample is associated with a first point of a pixilated screen. A second sample that follows the first sample is associated with a second point of the screen. A boundary of a rectangular line segment connecting the points is determined. For each pixel of the pixilated screen that has any portion inside the boundary of the rectangular line segment, a number of subpixels within the pixel that have any portion inside the boundary of the rectangular line segment is determined and that number of subpixels is correlated with an intensity value that is then associated with the pixel. Waveform data is displayed by painting pixels of the screen with the associated intensity values.

20 Claims, 8 Drawing Sheets

(56) References Cited

U.S. PATENT DOCUMENTS

| | | | |
|---|---|---|---|
| 2009/0198811 A1* | 8/2009 | Yasui et al. | 709/223 |
| 2009/0241958 A1* | 10/2009 | Baker, Jr. | 128/204.23 |
| 2010/0183310 A1* | 7/2010 | Suzuki et al. | 398/81 |
| 2010/0323608 A1* | 12/2010 | Sanhedrai et al. | 455/1 |
| 2011/0110486 A1* | 5/2011 | Bouhnik et al. | 378/8 |
| 2011/0241907 A1* | 10/2011 | Cordeiro | 341/20 |
| 2013/0004028 A1* | 1/2013 | Jones et al. | 382/118 |

\* cited by examiner

SYSTEMS AND METHODS FOR DISPLAYING DIGITIZED WAVEFORMS ON PIXILATED SCREENS

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Embodiments of the present technology generally relate to digitized waveforms that are displayed on pixilated screens. Certain embodiments relate to systems and methods of displaying digitized waveforms on pixilated screens.

Cardiologists spend much of their time looking at waveforms to determine the activity of the heart. The waveform is an analog signal that does not contain discrete values, but instead is a record of smooth changes over time. To display this signal on a computer monitor requires interpreting these discrete values in such a manner as to display a continuous line on the screen. This is further complicated by the fact that the screen is itself broken into discrete points, called pixels.

Starting with discrete waveform values for each screen location, it is possible to "connect the dots" and draw lines that form a visual representation of the signal. The initial algorithm that was used for drawing lines on a digital screen, known as the Bresenham algorithm, creates one-pixel wide lines between two points using linear-interpolation using only integers. The general outline of this algorithm has been used in drawing signal waveforms for as long as computer-assisted cardiology has been in practice. This routine runs very quickly, so at a time when processor power was very limited, this method was the most appropriate. Drawing signals using this method causes aliasing, a visual stair-step effect, because the line actually passes halfway between the pixels that are available for display. To combat this, a number of techniques exist to anti-alias waveform lines during the drawing process. These methods generally involve modulating the color of various pixels used to form the line, and require more processing in order to produce improved results.

A traditional cardiogram was plotted by means of an inked stylus moving across a piece of paper that was being dragged at a constant rate. Consequently, the baseline of the signal was thicker than the rises or falls, due to the ink flow rate being constant, but velocity changing depending on the movement of the stylus. This produced a very characteristic look that the cardiologist could use to help interpret the waveform.

Present systems do not provide this characteristic look, and do not allow a user to customize waveform display settings to control waveform line thicknesses. Also, present anti-aliasing techniques can require excessive processing, and may not provide desired results.

Thus, there is a need for improved systems and methods for displaying digitized waveforms on pixilated screens.

BRIEF SUMMARY OF THE INVENTION

Embodiments of the present technology provide systems, methods and computer-readable mediums encoded with computer instructions for displaying digitized waveforms on pixilated screens.

In certain embodiments, a method for displaying digitized waveform data on a pixilated screen includes: retrieving waveform data that exists as a plurality of sequential samples in a buffer; associating a first sample with a first point of a screen comprising a plurality of pixels; associating a second sample that follows the first sample with a second point of the pixilated screen; determining a boundary of a rectangular line segment connecting the first point and the second point; for each pixel of the pixilated screen that has any portion inside the boundary of the rectangular line segment, determining a number of subpixels within the pixel that have any portion inside the boundary of the rectangular line segment; for each pixel of the pixilated screen that has any portion inside the boundary of the rectangular line segment, correlating the number of subpixels within the pixel that have any portion inside the boundary of the rectangular line segment with an intensity value that is then associated with the pixel; and displaying waveform data by painting pixels of the screen with the associated intensity values.

In certain embodiments, the boundary of the rectangular line segment is determined using a rise angle of the rectangular line segment in combination with horizontal and vertical line width setting values.

In certain embodiments, a method further includes using a user interface to manually adjust a horizontal line width setting value that is used to determine the boundary of the rectangular line segment.

In certain embodiments, a method further includes using a user interface to manually adjust a vertical line width setting value that is used to determine the boundary of the rectangular line segment.

In certain embodiments, a method further includes using a user interface to manually and simultaneously adjust a horizontal line width setting value and a vertical line width setting value that are used to determine the boundary of the rectangular line segment.

In certain embodiments, the intensity value that is associated with each pixel is correlated using an intensity value map.

In certain embodiments, a method further includes obtaining the waveform data using an electrocardiography device.

In certain embodiments, a system for displaying digitized waveform data on a pixilated screen includes: a computer processor configured to retrieve waveform data that exists as a plurality of sequential samples in a buffer, the computer processor configured to associate a first sample with a first point of a screen comprising a plurality of pixels, the computer processor configured to associate a second sample that follows the first sample with a second point of the pixilated screen, the computer processor configured to determine a boundary of a rectangular line segment connecting the first point and the second point, for each pixel of the pixilated screen that has any portion inside the boundary of the rectangular line segment, the computer processor configured to determine a number of subpixels within the pixel that have any portion inside the boundary of the rectangular line segment, for each pixel of the pixilated screen that has any portion inside the boundary of the rectangular line segment, the computer processor configured to correlate the number of subpixels within the pixel that have any portion inside the boundary of the rectangular line segment with an intensity value that is then associated with the pixel; and the screen configured to display waveform data by painting pixels with the associated intensity values.

In certain embodiments, the computer processor is configured to determine the boundary of the rectangular line segment using a rise angle of the rectangular line segment in combination with horizontal and vertical line width setting values.

In certain embodiments, a system further includes a user interface configured to allow a user to manually adjust a horizontal line width setting value that is used to determine the boundary of the rectangular line segment.

In certain embodiments, a system further includes a user interface configured to allow a user to manually adjust a vertical line width setting value that is used to determine the boundary of the rectangular line segment.

In certain embodiments, a system further includes a user interface configured to allow a user to manually and simultaneously adjust a horizontal line width setting value and a vertical line width setting value that are used to determine the boundary of the rectangular line segment.

In certain embodiments, the computer processor is configured to use an intensity value map to correlate the intensity value with each pixel.

In certain embodiments, the computer processor is configured to obtain the waveform data using an electrocardiography device.

In certain embodiments, a non-transitory computer-readable storage medium is encoded with a set of instructions for execution on a processing device and associated processing logic, and the set of instructions includes: a first routine configured to retrieve waveform data that exists as a plurality of sequential samples in a buffer; a second routine configured to associate a first sample with a first point of a screen comprising a plurality of pixels; a third routine configured to associate a second sample that follows the first sample with a second point of the pixilated screen; a fourth routine configured to determine a boundary of a rectangular line segment connecting the first point and the second point, for each pixel of the pixilated screen that has any portion inside the boundary of the rectangular line segment; a fifth routine configured to determine a number of subpixels within the pixel that have any portion inside the boundary of the rectangular line segment; for each pixel of the pixilated screen that has any portion inside the boundary of the rectangular line segment, a sixth routine configured to correlate the number of subpixels within the pixel that have any portion inside the boundary of the rectangular line segment with an intensity value that is then associated with the pixel; and a seventh routine configured to display waveform data by painting pixels with the associated intensity values.

In certain embodiments, the fourth routine is configured to determine the boundary of the rectangular line segment using a rise angle of the rectangular line segment in combination with horizontal and vertical line width setting values.

In certain embodiments, the instructions further include an eighth routine configured to allow a user to manually adjust a horizontal line width setting value that is used to determine the boundary of the rectangular line segment.

In certain embodiments, the instructions further include an eighth routine configured to allow a user to manually adjust a vertical line width setting value that is used to determine the boundary of the rectangular line segment.

In certain embodiments, the instructions further include an eighth routine configured to allow a user to manually and simultaneously adjust a horizontal line width setting value and a vertical line width setting value that are used to determine the boundary of the rectangular line segment.

In certain embodiments, the sixth routine is configured to use an intensity value map to correlate the intensity value with each pixel.

The foregoing summary, as well as the following detailed description of embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF CERTAIN EMBODIMENTS

Embodiments of the present technology generally relate to digitized waveforms that are displayed on pixilated screens. Certain embodiments relate to systems and methods of displaying digitized waveforms on pixilated screens.

Embodiments of the present technology provide for drawing digitized waveforms on a pixilated screen in an anti-aliased manner, with different line thickness adjustments for a horizontal line (baseline) vs. a vertical line (spike). In certain embodiments, the system continuously adjusts the thickness of each line segment based on the "velocity" that a traditional stylus would have had in the pen and ink model. In certain embodiments, a user interface can allow a user to set parameters within a set range to produce waveform characteristics that help them see the waveform morphology.

While embodiments described herein are discussed in connection with waveforms relating to electrocardiography, pressures, surface leads and vitals, the inventions disclosed herein are not limited to such applications. In other words, the inventions herein can be used in connection with any type of digitized waveform that is displayed on a pixilated screen.

Figure 1:
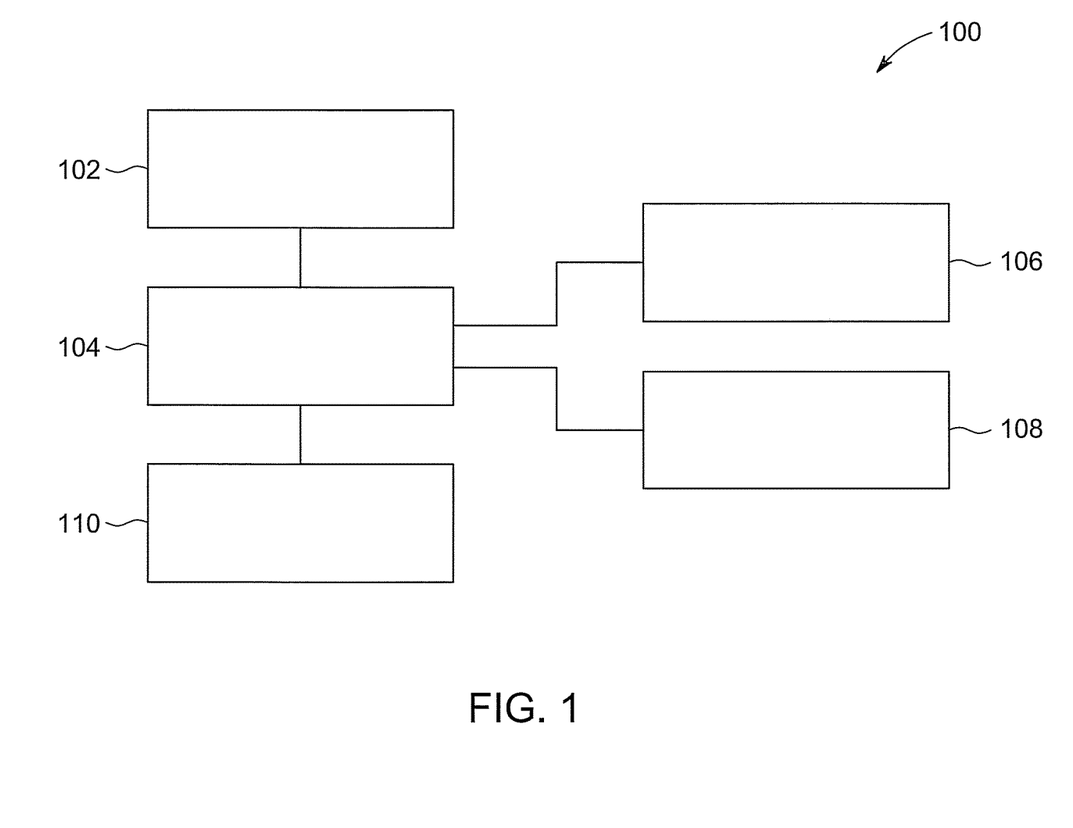
FIG. 1 illustrates a system for displaying digitized waveform data on a pixilated screen used in accordance with an embodiment of the present technology.

FIG. 1 illustrates a system 100 for displaying digitized waveform data on a pixilated screen used in accordance with an embodiment of the present technology. System 100 includes waveform capture device 102, computer processor 104, user interface 106, data storage 108 and pixilated screen 110. Waveform capture device 102 can be any device that can obtain waveform data from a subject, such as an electrocardiography device, for example. Computer processor 104 can be any processing device capable of executing computer-readable code. User interface 106 can include a graphical user interface, a mouse, a keyboard, a stylus and/or any other device that can allow a user to provide an input to computer processor 104. Data storage 108 can include any device capable of storing data, including data arranged in a database and/or an electronic medical record, for example. Pixilated screen 110 can include a computer monitor, a LCD display and/or any other device that uses a pixilated screen to display digitized waveform data. Waveform capture device 102 is operably connected to computer processor 104, which is operably connected to user interface 106, data storage 108 and pixilated screen 110. In certain embodiments, the elements 102-110 can be implemented in any combination of stand-alone components and/or integrated components.

Figure 2:
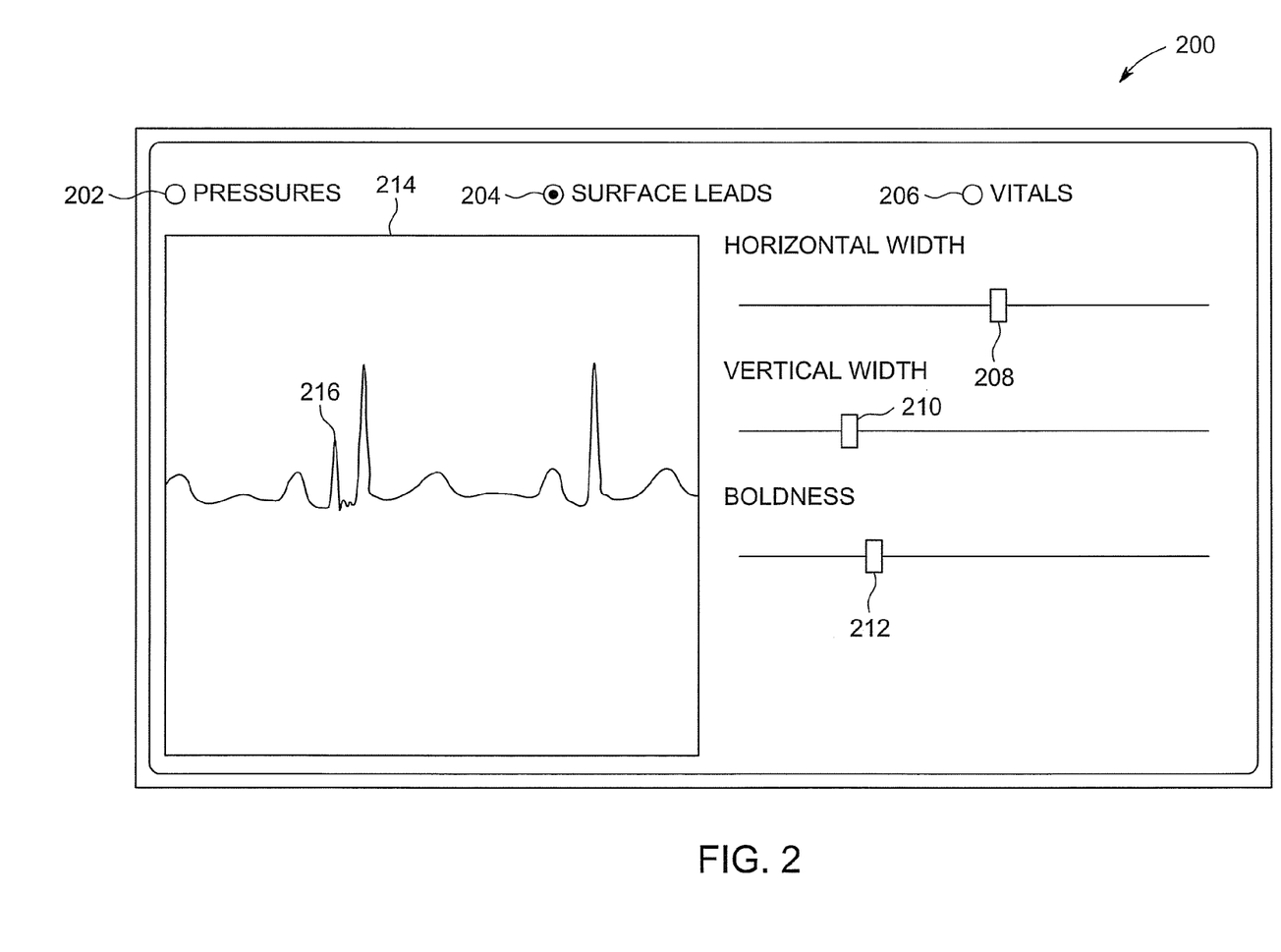
FIG. 2 depicts a user interface used in accordance with embodiments of the present technology that is configured to allow a user to customize the manner in which digitized waveform data is displayed on a pixilated screen.

FIG. 2 depicts a user interface 200 used in accordance with embodiments of the present technology that is configured to allow a user to customize the manner in which digitized waveform data is displayed on a pixilated screen. In certain embodiments, user interface 200 can be operably connected to computer processor 104. User interface 200 includes radio buttons 202, 204, 206, sliders 208, 210 and 212 and display window 214. Display window 214 is configured to display a sample waveform 216 that depicts the manner in which a selected type of waveform data will be displayed on a pixilated screen.

Sliders 208, 210 and 212 are configured to allow a user to change the manner in which digitized waveform data will be displayed on a pixilated screen. Slider 208 is configured to allow adjustment of the width of horizontal line segments in a waveform, such that the horizontal line segments can appear thicker or thinner on a pixilated screen. Slider 210 is configured to allow adjustment of the width of vertical line segments in a waveform, such that the vertical line segments can appear thicker or thinner on a pixilated screen. Slider 212 is configured to allow adjustment of the overall boldness of a waveform, thereby simultaneously adjusting the widths of both horizontal and vertical line segments in the waveform, such that both the horizontal and vertical line segments can appear thicker or thinner on a pixilated screen while maintaining relative thickness of the horizontal and vertical line segments. In operation, a user can move any of the sliders in order to change the above waveform display properties and the sample waveform 216 depicted in display window 214 will be updated in substantially real-time to reflect the changed waveform display properties.

Each radio button is associated with a different type of waveform data. Radio button 202 is associated with waveform data obtained using pressure sensors. Selecting radio button 202 can display a sample waveform that depicts the manner in which waveform data obtained using pressure sensors will be displayed on a pixilated screen. Radio button 204 is associated with waveform data obtained using surface leads. Selecting radio button 204 can display a sample waveform that depicts the manner in which waveform data obtained using surface leads will be displayed on a pixilated screen. Radio button 206 is associated with waveform data obtained using vital sign sensors. Selecting radio button 206 can display a sample waveform that depicts the manner in which waveform data obtained using vital sign sensors will be displayed on a pixilated screen.

In certain embodiments, waveform display settings can be saved in data storage 108 and can be associated with a user, a group of users and/or a hospital department, for example. In such embodiments, stored waveform display settings can be loaded automatically based on the user, group of users and/or hospital department.

Figure 3:
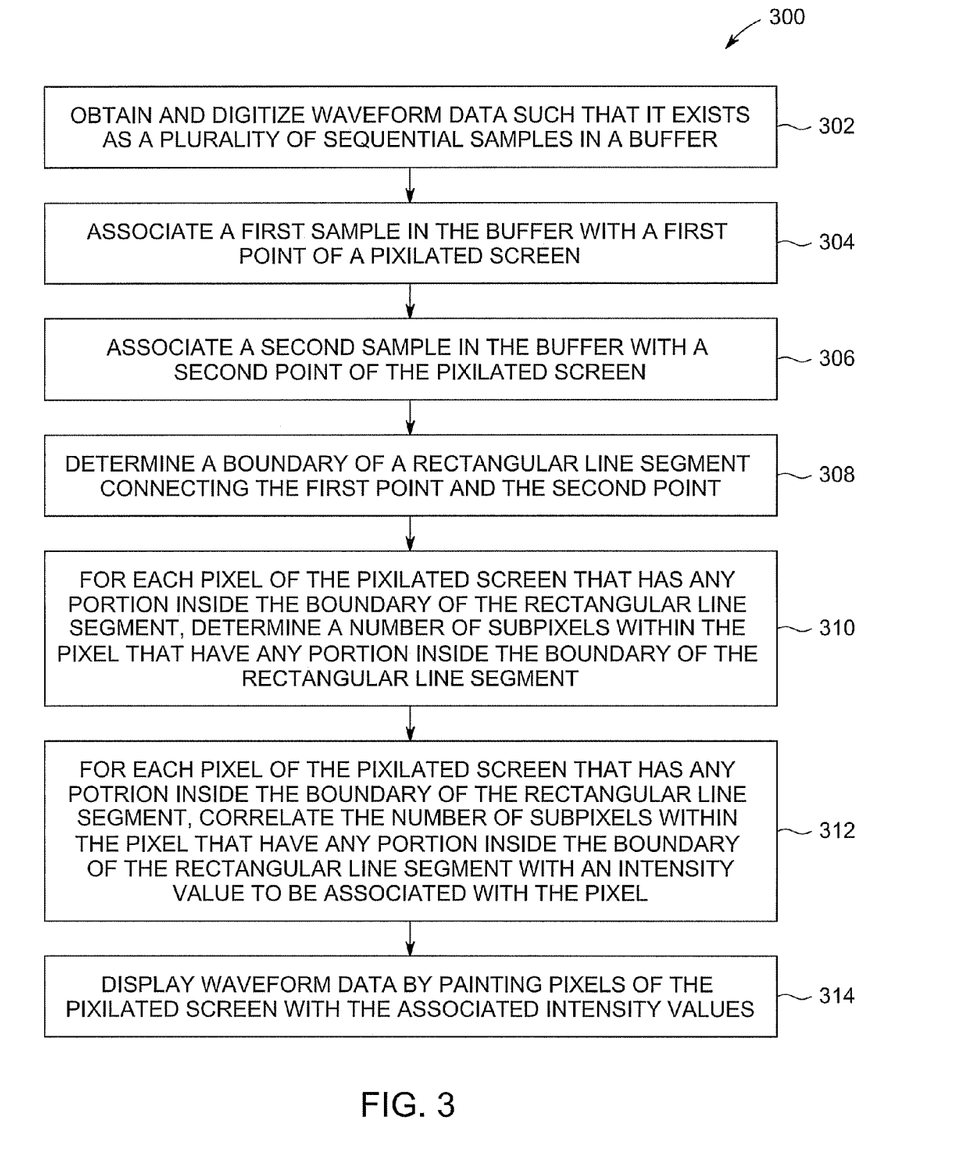
FIG. 3 illustrates a method for displaying digitized waveform data on a pixilated screen used in accordance with an embodiment of the present technology.

FIG. 3 illustrates a method 300 for displaying digitized waveform data on a pixilated screen used in accordance with an embodiment of the present technology. At 302, waveform data is obtained from a subject and digitized. For example, in certain embodiments, sensors that are pressure sensors, surface leads and/or vital sign sensors can be used in combination with an electrocardiography device in order to obtain waveform data for a patient. The waveform data can be digitized such that it exists in the form of a plurality of sequential samples in a buffer. Displaying the samples in order can reproduce the waveform.

At 304, a first sample in a buffer is associated with a first point of a pixilated screen. For example, the first sample can be associated with coordinates (x, y) on a two-dimensional coordinate plane of a pixilated screen with a horizontal x-axis (representing time) and a vertical y-axis. For example, the first sample can be associated with coordinates coordinates (0, 0.0), and can be associated with a first point of a pixilated screen that corresponds to such a coordinate. In certain embodiments, the x-coordinates are always integers, and the y-coordinate s can be non-integers with decimal places.

At 306, a second sample in the buffer that is the next sequential sample after the first sample is associated with a second point of the pixilated screen. For example, in certain embodiments, a second sample in a buffer can have coordinates (1, 1.0), and can be associated with a second point of the pixilated screen that corresponds to such a coordinate. In certain embodiments, sample rate, which corresponds to the amount of time between obtaining data for sequential samples (measured, for example, in samples/second), and/or sweep speed, which corresponds to the speed at which waveform data is displayed across a pixilated screen (measured, for example, in millimeters/second), can be used in connection with associating the second sample in the buffer with a second point of the pixilated screen.

At 308, a boundary of a rectangular line segment connecting the first point and the second point of the pixilated screen can be determined. In certain embodiments, for example, rise angle of the rectangular line segment in combination with horizontal and vertical line width setting values can be used to determine the boundary of the rectangular line segment. Such an embodiment will be described in more detail below in connection with FIG. 4. In certain embodiments, for example, horizontal and/or vertical line width setting values can be those selected by a user using the user interface 200 described above, or a similarly configured user interface.

At 310, for each pixel of the pixilated screen that has any portion inside the boundary of the rectangular line segment, a number of subpixels within the pixel that have any portion inside the boundary of the rectangular line segment is determined. At 312, for each pixel of the pixilated screen that has any portion inside the boundary of the rectangular line segment, the number of subpixels within the pixel that have any portion inside the boundary of the rectangular line segment is correlated with an intensity value to be associated with the pixel. At 314, waveform data is displayed on the pixilated screen by painting pixels with associated intensity values. An embodiment employing steps 310-314 is described in further detail below in connection with FIGS. 5-6.

Figure 4:
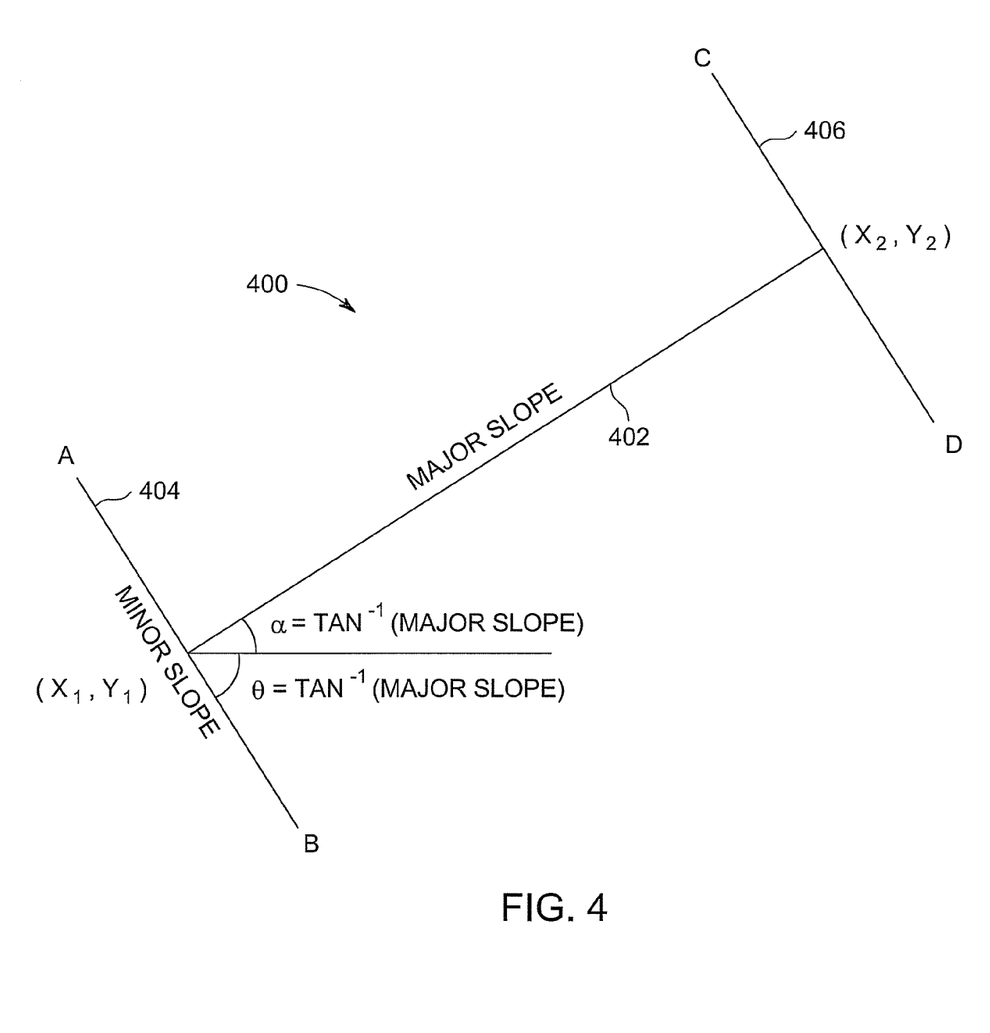
FIG. 4 is a diagram depicting a technique for calculating a boundary of a rectangular line segment between two points used in accordance with embodiments of the present technology.

FIG. 4 is a diagram 400 depicting a technique for calculating a boundary of a rectangular line segment used in accordance with embodiments of the present technology. In FIG. 4, first point (x1, y1) and second point (x2, y2) are connected by line 402. The slope of line 402 is referred to as the major slope. Line 404 runs through first point (x1, y1) perpendicular to line 402. The slope of line 404 is referred to as the minor slope. Points a, b, c and d are the bounding corners of the rectangular line segment, which has a width equal to the distance between a and b, which is also equal to the distance between c and d.

When first point (x1, y1)=(0, 0.0) and second point (x2, y2)=(1, 1.0), the following values follow.

Major slope=(y2−y1)/(x2−x1)=1.0

Minor slope=−1.0/major slope=−1.0

θ=arc tan(Minor slope)=−0.785 radians

α=arc tan(Major slope)=0.785 radians

Segment width(w)=(horizontal line width value(Wh)
*vertical line width value(Wv))*|2α/π|=1.5 for
Wh=2.0 and Wv=1.0 a=(x1−(w/2)cos θ,y1−(w/2)cos θ*Minor slope)=(−0.53,0.53)

b=(x1+(w/2)cos θ,y1+(w/2)cos θ*Minor slope)=(0.53,−0.53)

c=(x2−(w/2)cos θ,y2−(w/2)cos θ*Minor slope)=(0.47, 1.53)

d=(x2+(w/2)cos θ,y2+(w/2)cos θ*Minor slope)=(1.53, 0.47)

The boundary of a rectangular line segment with bounding corners a, b, c and d can be depicted graphically, representing the desired waveform segment between two points. However, such rectangular line segments do not align perfectly with the pixels in the grid of a pixilated screen. Rather, in many instances, each pixel that has any portion inside the boundary of the rectangular line segment will not have the entire pixel inside the boundary of the rectangular line segment. It has been found that selecting an intensity value for a pixel based on the amount of the pixel that is within the boundary of the rectangular line segment can provide for improved anti-aliasing of digitized waveform data being displayed on a pixilated screen.

Figure 5:
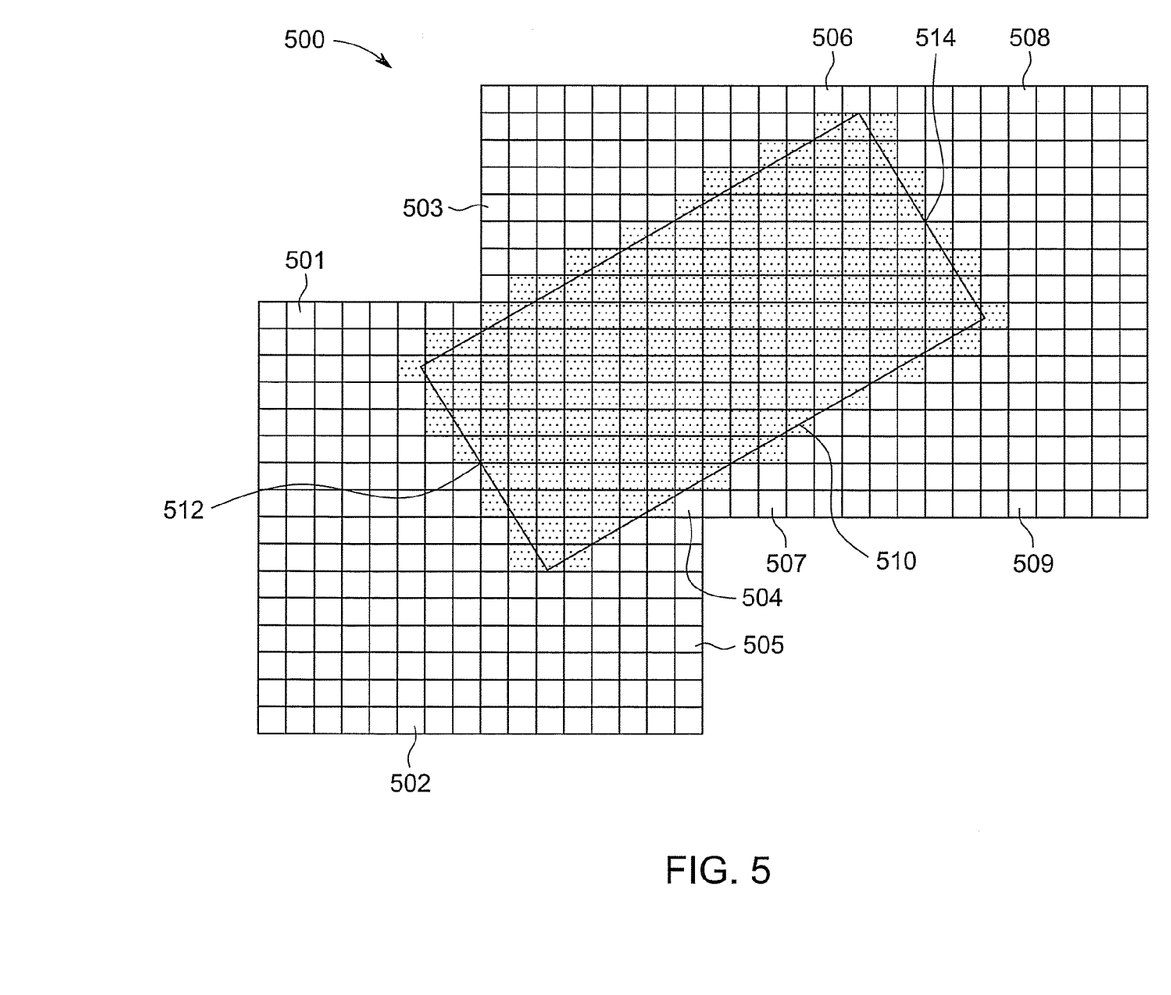
FIG. 5 depicts a rectangular line segment between two points laid over a pixilated screen with each pixel subdivided into subpixels used in accordance with embodiments of the present technology.

FIG. 5 depicts a rectangular line segment between two points 512, 514 laid over a pixilated screen with each pixel 501-509 subdivided into subpixels. The rectangular line segment with boundary 510 is between first point 512 at (1, 1.25) and second point 514 at (3, 2.375). Each of the pixels 501-509 are square and are subdivided into 64 equally-sized, square subpixels. In other words, each pixel 501-509 is depicted as an 8×8 square including 64 equally-sized, square subpixels. Each subpixel that has any portion inside boundary 510 is shaded.

Figure 6:
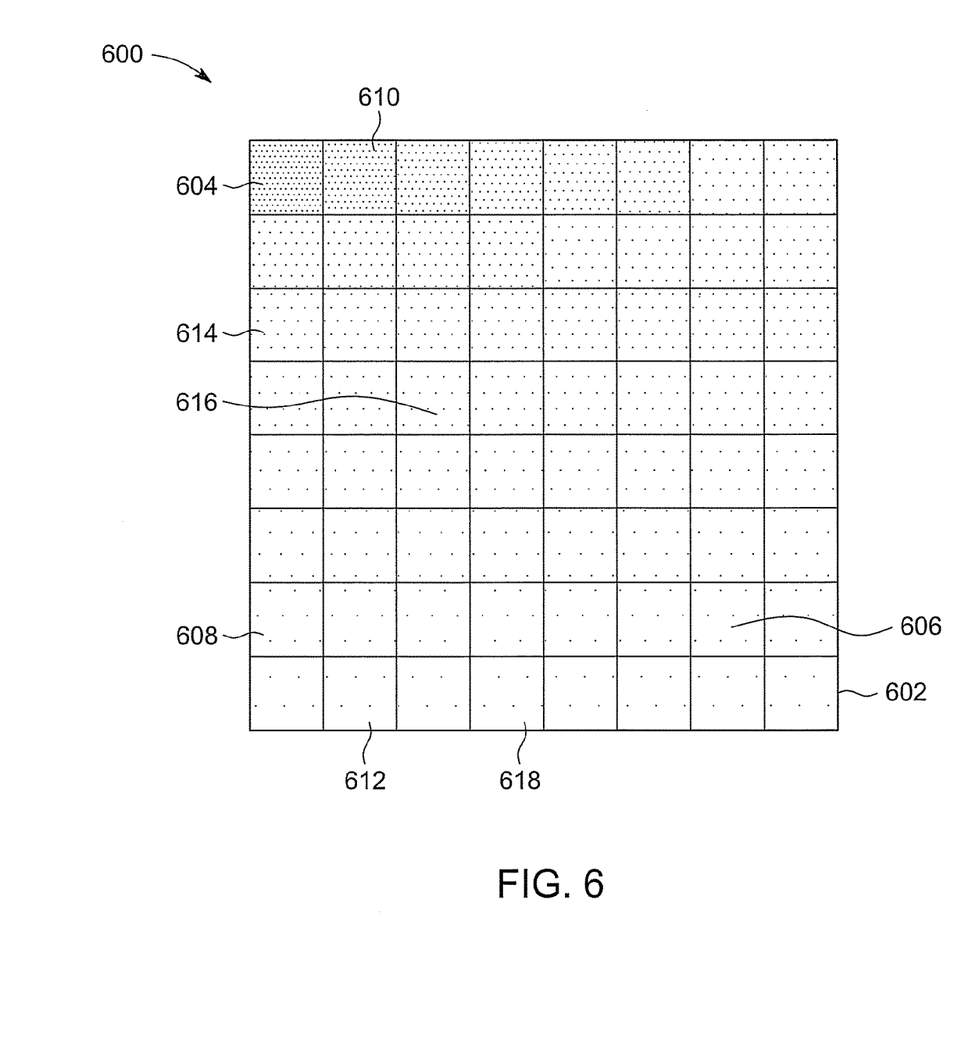
FIG. 6 depicts an intensity value map used in accordance with embodiments of the present technology.

The number of shaded subpixels in each pixel can be used to determine an intensity value for the pixel. For example, FIG. 6 depicts an intensity value map 600 used in accordance with embodiments of the present technology. Intensity value map 600 includes a lightest intensity value 602, which can be associated with a pixel that has only one subpixel having a portion inside a boundary of a rectangular line segment. Intensity value map 600 also includes a darkest intensity value 604, which can be associated with a pixel that has all subpixels having a portion inside the boundary of the rectangular line segment. Intensity value map 600 includes sixty-two other intensity values that can be associated with a pixel that has a given number of subpixels having a portion inside the boundary of the rectangular line segment.

Referring back to FIG. 5, pixel 501 includes ten shaded subpixels and thus would be associated with intensity value 606 from intensity value map 600. Pixel 502 includes zero shaded subpixels, and thus would be associated with no intensity value. Pixel 503 includes sixteen shaded subpixels and thus would be associated with intensity value 608 from intensity value map 600. Pixel 504 includes sixty-three shaded subpixels and thus would be associated with intensity value 610 from intensity value map 600. Pixel 505 includes seven shaded subpixels and thus would be associated with intensity value 612 from intensity value map 600. Pixel 506 includes forty-eight shaded subpixels and thus would be associated with intensity value 614 from intensity value map 600. Pixel 507 includes thirty-eight shaded subpixels and thus would be associated with intensity value 616 from intensity value map 600. Pixels 508 and 509 each include five shaded subpixels and thus would be associated with intensity value 618 from intensity value map 600. The waveform data for the rectangular line segment depicted in FIG. 5 can be displayed on a pixilated screen by painting pixels 501-509 with the associated intensity values. The process can be repeated for subsequent rectangular line segments.

In certain embodiments, subsequent rectangular line segments can overlap within a given pixel. In such embodiments, a pixel may not be assigned an intensity value until both rectangular line segments are evaluated, such that subpixels included in either the first rectangular line segment and/or the second rectangular line segment will be counted as falling within a rectangular line segment. In certain embodiments, a pixel will not be assigned an intensity value until all rectangular line segments that could possibly overlap with the pixel have been evaluated.

In certain embodiments, pixels can be subdivided into greater or fewer subpixels than in the examples herein. In such embodiments, a value intensity map can have a corresponding number of intensity value options. In certain embodiments, a value intensity map can have fewer intensity value options than there are subpixels.

Certain embodiments of the present invention may omit one or more of the steps and/or perform the steps in a different order than the order listed in connection with FIGS. 3-6. For example, some steps may not be performed in certain embodiments of the present invention. As a further example, certain steps may be performed in a different temporal order, including simultaneously, than listed above.

One or more of the steps of the method 300 may be implemented alone or in combination in hardware, firmware, and/or as a set of instructions in software, for example. Certain embodiments may employ the system 100 described herein including processor 104 to achieve the method steps. Certain embodiments may be provided as a set of instructions residing on a tangible, non-transitory computer-readable medium, such as a memory, hard disk, DVD, or CD, for execution on a general purpose computer or other processing device. For example, certain embodiments provide a non-transitory computer-readable storage medium encoded with a set of instructions for execution on a processing device and associated processing logic, wherein the set of instructions includes a routine(s) configured to provide the functions described in connection with the method 300.

Applying the method 300 as described above, and/or in light of the techniques and systems described herein, can provide a technical effect of improving visual quality of digitized waveforms displayed on pixilated screens, and can improve user control over waveform display settings, such as horizontal and vertical line thickness.

Certain image data acquired, analyzed and displayed in connection with techniques described herein represent the function of human anatomy, such as the heart, for example. In other words, outputting a visual display based on such data comprises a transformation of underlying subject matter (such as an article or materials) to a different state.

Figure 7:
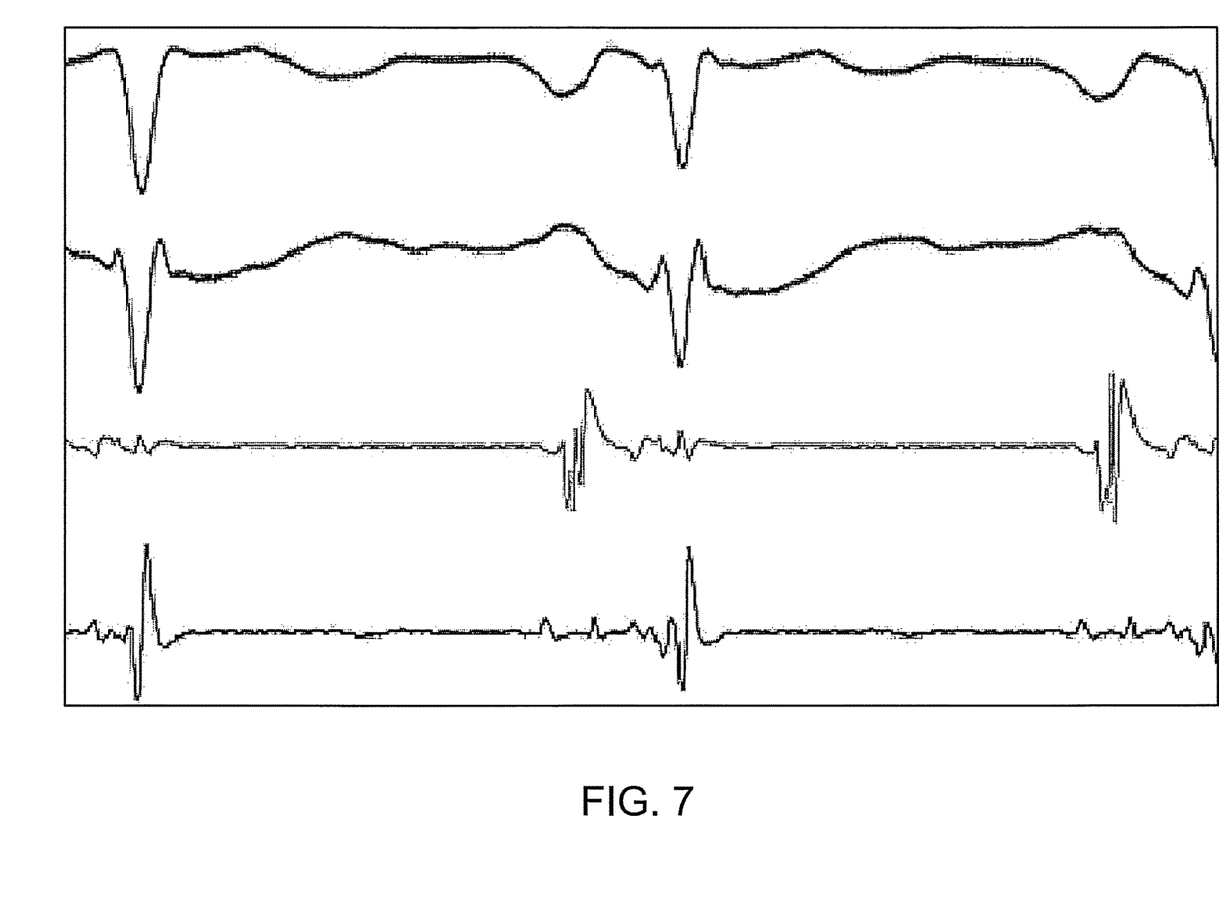
FIG. 7 depicts digitized waveform data being displayed on a pixilated screen in accordance with embodiments of the present technology.
Figure 8:
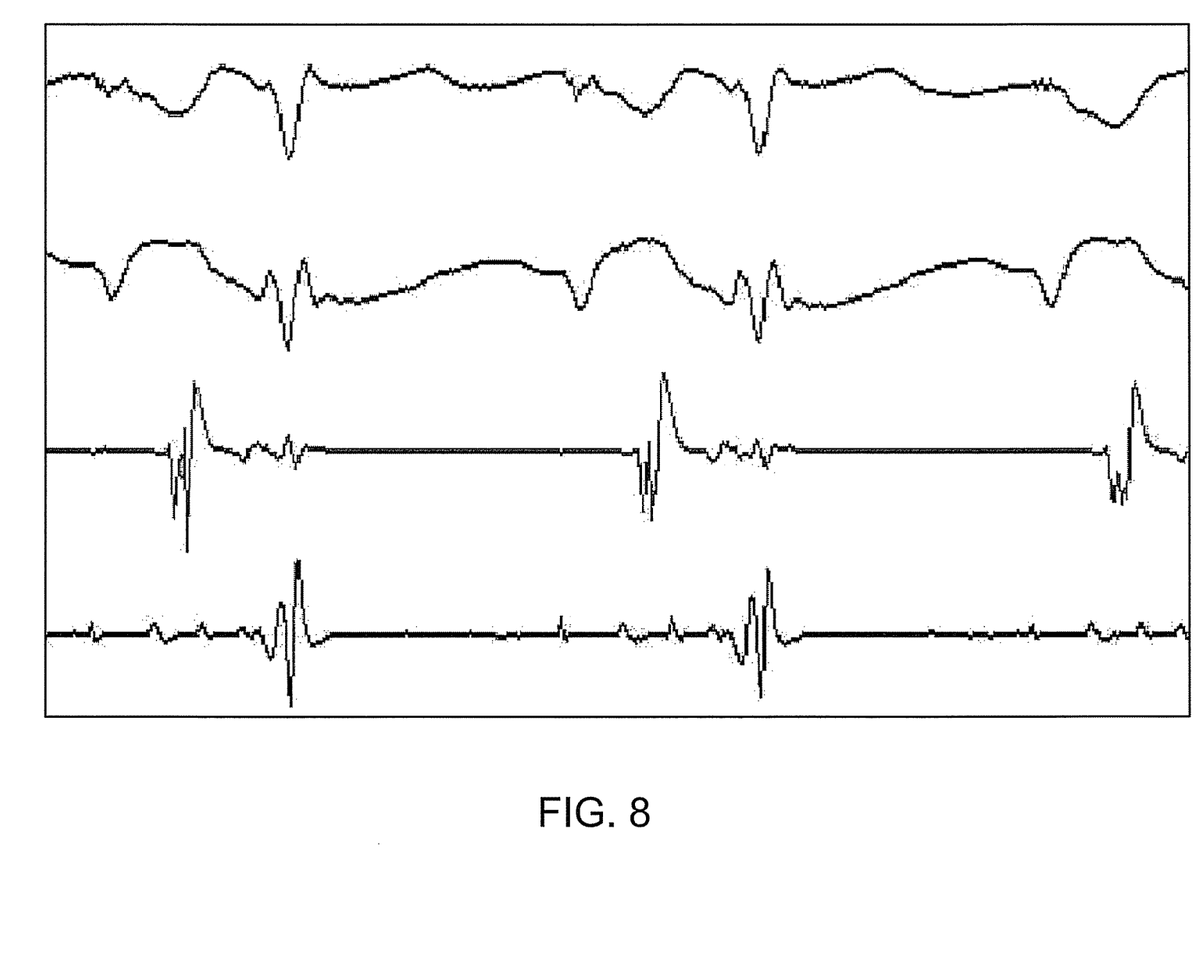
FIG. 8 depicts digitized waveform data being displayed on a pixilated screen using known methods.

FIG. 7 depicts digitized waveform data being displayed on a pixilated screen in accordance with embodiments of the present technology. FIG. 8 depicts digitized waveform data being displayed on a pixilated screen using known methods. Comparing FIG. 7 and FIG. 8, improved visual quality that can be achieved using an embodiment of the present technology is evident.

While the invention has been described with reference to embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for displaying digitized waveform data on a pixilated screen comprising:
   retrieving waveform data that exists as a plurality of sequential samples in a buffer;
   associating a first sample with a first point of a screen comprising a plurality of pixels;
   associating a second sample that follows the first sample with a second point of the pixilated screen;
   determining a boundary of a rectangular line segment connecting the first point and the second point;
   for each pixel of the pixilated screen that has any portion inside the boundary of the rectangular line segment, determining a number of subpixels within the pixel that have any portion inside the boundary of the rectangular line segment;
   for each pixel of the pixilated screen that has any portion inside the boundary of the rectangular line segment, correlating the number of subpixels within the pixel that have any portion inside the boundary of the rectangular line segment with an intensity value that is then associated with the pixel; and
   displaying waveform data by painting pixels of the screen with the associated intensity values.

2. The method of claim 1, wherein the boundary of the rectangular line segment is determined using a rise angle of the rectangular line segment in combination with horizontal and vertical line width setting values.

3. The method of claim 1, further comprising using a user interface to manually adjust a horizontal line width setting value that is used to determine the boundary of the rectangular line segment.

4. The method of claim 1, further comprising using a user interface to manually adjust a vertical line width setting value that is used to determine the boundary of the rectangular line segment.

5. The method of claim 1, further comprising using a user interface to manually and simultaneously adjust a horizontal line width setting value and a vertical line width setting value that are used to determine the boundary of the rectangular line segment.

6. The method of claim 1, wherein the intensity value that is associated with each pixel is correlated using an intensity value map.

7. The method of claim 1, further comprising obtaining the waveform data using an electrocardiography device.

8. A system for displaying digitized waveform data on a pixilated screen comprising:
   a computer processor configured to retrieve waveform data that exists as a plurality of sequential samples in a buffer,
   the computer processor configured to associate a first sample with a first point of a screen comprising a plurality of pixels,
   the computer processor configured to associate a second sample that follows the first sample with a second point of the pixilated screen,
   the computer processor configured to determine a boundary of a rectangular line segment connecting the first point and the second point,
   for each pixel of the pixilated screen that has any portion inside the boundary of the rectangular line segment, the computer processor configured to determine a number of subpixels within the pixel that have any portion inside the boundary of the rectangular line segment,
   for each pixel of the pixilated screen that has any portion inside the boundary of the rectangular line segment, the computer processor configured to correlate the number of subpixels within the pixel that have any portion inside the boundary of the rectangular line segment with an intensity value that is then associated with the pixel; and
   the screen configured to display waveform data by painting pixels with the associated intensity values.

9. The system of claim 8, wherein the computer processor is configured to determine the boundary of the rectangular line segment using a rise angle of the rectangular line segment in combination with horizontal and vertical line width setting values.

10. The system of claim 8, further comprising a user interface configured to allow a user to manually adjust a horizontal line width setting value that is used to determine the boundary of the rectangular line segment.

11. The system of claim 8, further comprising a user interface configured to allow a user to manually adjust a vertical line width setting value that is used to determine the boundary of the rectangular line segment.

12. The system of claim 8, further comprising a user interface configured to allow a user to manually and simultaneously adjust a horizontal line width setting value and a vertical line width setting value that are used to determine the boundary of the rectangular line segment.

13. The system of claim 8, wherein the computer processor is configured to use an intensity value map to correlate the intensity value with each pixel.

14. The system of claim 8, wherein the computer processor is configured to obtain the waveform data using an electrocardiography device.

15. A non-transitory computer-readable storage medium encoded with a set of instructions for execution on a processing device and associated processing logic, wherein the set of instructions includes:
   a first routine configured to retrieve waveform data that exists as a plurality of sequential samples in a buffer;
   a second routine configured to associate a first sample with a first point of a screen comprising a plurality of pixels;
   a third routine configured to associate a second sample that follows the first sample with a second point of the pixilated screen;
   a fourth routine configured to determine a boundary of a rectangular line segment connecting the first point and the second point;
   for each pixel of the pixilated screen that has any portion inside the boundary of the rectangular line segment, a fifth routine configured to determine a number of subpixels within the pixel that have any portion inside the boundary of the rectangular line segment;

for each pixel of the pixilated screen that has any portion inside the boundary of the rectangular line segment, a sixth routine configured to correlate the number of sub-pixels within the pixel that have any portion inside the boundary of the rectangular line segment with an intensity value that is then associated with the pixel; and a seventh routine configured to display waveform data by painting pixels with the associated intensity values.

16. The medium and instructions of claim 15, wherein the fourth routine is configured to determine the boundary of the rectangular line segment using a rise angle of the rectangular line segment in combination with horizontal and vertical line width setting values.

17. The medium and instructions of claim 15, further comprising an eighth routine configured to allow a user to manually adjust a horizontal line width setting value that is used to determine the boundary of the rectangular line segment.

18. The medium and instructions of claim 15, further comprising an eighth routine configured to allow a user to manually adjust a vertical line width setting value that is used to determine the boundary of the rectangular line segment.

19. The medium and instructions of claim 15, further comprising an eighth routine configured to allow a user to manually and simultaneously adjust a horizontal line width setting value and a vertical line width setting value that are used to determine the boundary of the rectangular line segment.

20. The medium and instructions of claim 15, wherein the sixth routine is configured to use an intensity value map to correlate the intensity value with each pixel.

\* \* \* \* \*